United States Patent
Aouad et al.

(10) Patent No.: US 7,414,158 B2
(45) Date of Patent: Aug. 19, 2008

(54) PROCESS FOR EPIMERISING CYCLOHEXENYL KETONES AND ITS APPLICATION IN ALDOL CONDENSATION PROCESS

(75) Inventors: Yousef Georges Aouad, Cincinnati, OH (US); Daniel Martin Bourgeois, Mason, OH (US); Gregory Scot Miracle, Hamilton, OH (US); Jean Wevers, Steenhuffel (BE); Harambage Quintas Nimal Gunaratne, Belfast (GB); Kenneth Richard Seddon, Donaghadee (GB); Eva Boros, Belfast (GB); Suhas Prabhaker Katdore, Pune (IN); Tayeb Belhocine, Belfast (GB)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 11/880,509

(22) Filed: Jul. 23, 2007

(65) Prior Publication Data

US 2008/0021246 A1    Jan. 24, 2008

Related U.S. Application Data

(60) Provisional application No. 60/832,910, filed on Jul. 24, 2006.

(51) Int. Cl.
*C07C 45/66* (2006.01)
*C07C 45/67* (2006.01)
(52) U.S. Cl. ...................... 568/338; 568/341
(58) Field of Classification Search ............ 568/338, 568/341
See application file for complete search history.

(56) References Cited

U.S. PATENT DOCUMENTS

| 4,198,309 A | 4/1980 | Mookherjee et al. |
| 6,320,083 B1 | 11/2001 | Saleh |
| 6,552,232 B2 | 4/2003 | Mehnert et al. |
| 6,822,121 B2 | 11/2004 | Watanabe et al. |
| 6,924,341 B2 | 8/2005 | Mays et al. |
| 2004/0077519 A1 | 4/2004 | Price et al. |
| 2004/0097755 A1 | 5/2004 | Abbott et al. |
| 2006/0128996 A1 | 6/2006 | Vaultier et al. |

FOREIGN PATENT DOCUMENTS

| WO | WO 01/81426 A1 | 11/2001 |
| WO | WO 2006/072775 A1 | 7/2006 |
| WO | WO 2006/072785 A2 | 7/2006 |

OTHER PUBLICATIONS

Torii, S., et al., "Synthetic Chemistry of Damascenones and Damascones," Koryo, No. 125, 1979, pp. 47-60.
"Sterochemistry of electrophilic substitution of (+)-3-carene: Prins and Friedel-Crafts-acetylation reactions" Tetrehedron vol. 42, 1968, pp. 1385-1395, XP002466906, Elsevier Science Publishers, Amsterdam, pp. 1386-1387, p. 1393.
L.F. Fieser, M. Fieser: "Reagents for Organic Synthesis", 1967, John Wiley and Sons, Inc., New York, London, Sydney, XP002466907, pp. 1075-1081.

*Primary Examiner*—Sikarl A Witherspoon
(74) *Attorney, Agent, or Firm*—Stephen T. Murphy; Kim William Zerby

(57) ABSTRACT

Processes for producing intermediate materials used for perfumery, specifically, epimerized cyclohexenyl ketones, are disclosed. Processes for employing the epimerising reaction in an Aldol condensation reaction are also disclosed.

25 Claims, No Drawings

PROCESS FOR EPIMERISING CYCLOHEXENYL KETONES AND ITS APPLICATION IN ALDOL CONDENSATION PROCESS

CROSS REFERENCE TO RELATED APPLICATIONS

This application claims priority under 35 U.S.C. §119(e) to U.S. Provisional Application Ser. No. 60/832,910 filed Jul. 24, 2006.

FIELD OF THE INVENTION

The present invention relates to processes for producing intermediate materials used for perfumery, specifically, epimerised cyclohexenyl ketones. The present invention also relates to processes for employing the epimerizing reaction in an Aldol condensation process.

BACKGROUND OF THE INVENTION

In the perfumery art, there is a considerable need for fragrant materials having fruity or flowery notes. Representative fragrant materials having fruity floral notes are such as δ-, α- and β-damascone. These damascone isomers have their own odor notes, respectively, while they have a fruity floral note basically. They are used differently according to their application purposes.

Damascones have three double-bond-depending isomers as described below.

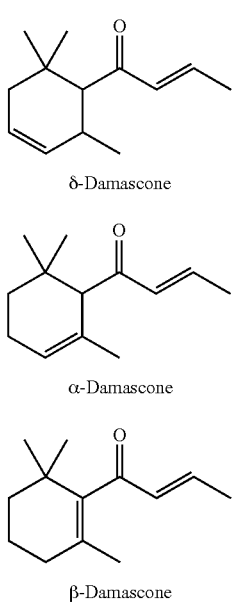

δ-Damascone (2a)

α-Damascone (2b)

β-Damascone (2c)

A large number of production processes for these damascone isomers have been reported, for example, in "Review" (Shigeru Torii, et al., Koryo, No. 125, 47-60 (1979)). Among them, a production process of α-, β- and δ-damascone represented by the following reaction

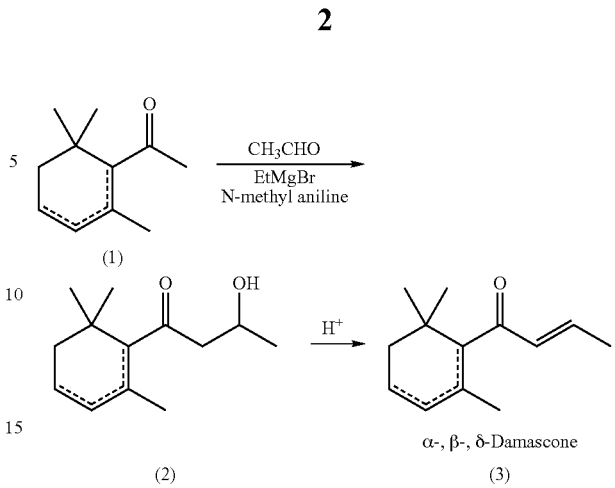

α-, β-, δ-Damascone (3)

wherein any one of dotted lines means a double bond.

The synthesis of α-, β- and δ-damascone involves two basic steps, namely, a Diels-Alder cycloaddition and an aldol condensation. The Diels-Alder cycloaddition produces 2,6,6-trimethylcyclohexenyl methyl ketone, from which damascones can be formed via further reaction steps, typically involving (a) epimerisation of cis- to trans-cycloadduct via enolate formation, (b) thermodynamic enolate addition to ethanal(acetaldehyde) to yield the corresponding aldol product and (c) dehydration of the aldol product to yield damascone.

2,6,6-Trimethylcyclohexenyl methyl ketone (1) is a useful compound as an intermediate for the synthesis of α-, β- and δ-damascone. It can be synthesized by a Diels-Alder reaction between 1,3-pentadiene and mesityl oxide as shown in the following reaction scheme:

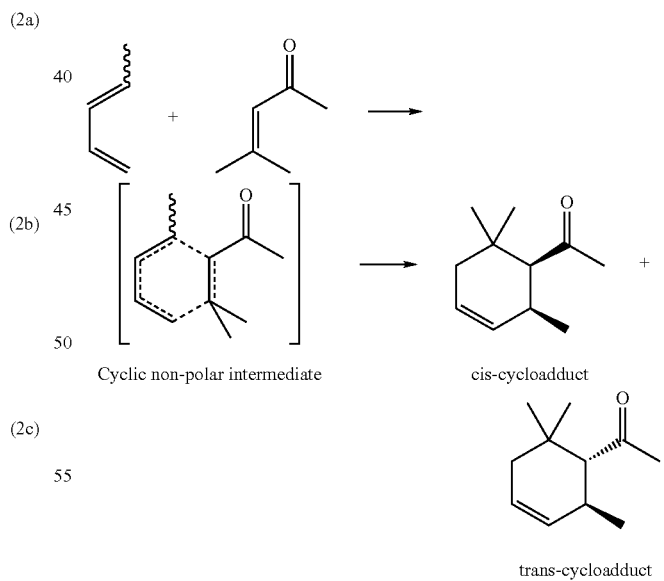

Typically, more cis-cycloadduct than trans-cycloadduct is produced.

There is a need for new synthesis processes to improve the control of stereochemistry of the cycloadducts. There is also a need to have new synthesis processes to improve the yield of the desired damascone products.

SUMMARY OF THE INVENTION

The present invention provides a process for epimerising the cis-cycloadduct to the trans-cycloadduct. Specifically, the present invention provides a process for epimerising the cycloadduct using hydride catalysts. Furthermore, the process is conducted in the presence of a ligand having at least two heteroatoms independently selected from O, N and S.

Alternatively, the present invention provides a process for epimerising the cycloadduct using metal hydride catalysts and an ionic liquid medium. Furthermore, the process is conducted in the presence of a ligand having at least two heteroatoms independently selected from O, N and S. In addition, the ionic liquid may contain a tethered functionality, which may function as a ligand The present invention also provides a process employing the above epimerising reaction in an aldol addition reaction with an aldehyde to produce a P-hydroxy alkyl cyclohexenyl ketone.

Additional embodiments, objects and advantages will be more fully apparent in view of the following detailed description.

DETAILED DESCRIPTION OF THE INVENTION

Epimerization Process

The present invention provides a novel process for epimerizing an epimerizable compound. Specifically, 2,6,6-trimethylcyclohexenyl methyl ketone is used as the starting material suitable for use in the epimerization process of the present invention. It is synthesised by the reaction scheme described above, more specifically, by the Diels-Alder reaction between 1,3-pentadiene and mesityl oxide in the presence of a catalyst, such as aluminium(III) chloride.

The epimerizing process of the present invention involves the step of contacting cyclohexenyl methyl ketone with a metal hydride catalyst, specifically hydrides of Group 1 and Group 2 metals, including but not limited to NaH, KH, LiH, $CaH_2$, $MgH_2$, and the like.

Although the reaction rate increases with the amount of catalyst, economic and safety factors should be considered as well. Hence, it is typical to use an amount of catalyst in the range from about 50% to about 95%, preferably at least about 65% and more preferably at least about 80%, by weight of the reaction mixture.

The reaction temperature varies, depending on the catalyst, the presence of ligands containing ether functionality and concentration of starting materials. Typically, the reaction temperature ranges from about 25 to about 80° C.

A proper amount of solvent may be used in conducting the epimerization reaction. Typically, solvent comprises from about 50% to about 95% by weight of the reaction mixture. Suitable solvents include, but are not limited to, ethers and ionic liquids.

In one embodiment, the reaction is conducted in the presence of a ligand that has at least two heteroatoms independently selected from an oxygen atom (O), nitrogen atom (N) and sulfur atom (S). Exemplary ligands include crown ethers, specifically 18-crown-6 ether having the structure as shown below:

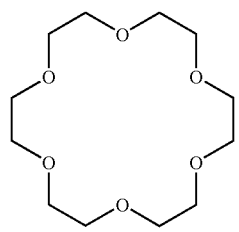

When crown ether is used, the reaction temperature is preferably from about 25° C. to 80° C. The amount of ligand-containing material typically ranges from about 25% to about 50% by weight of the reaction mixture.

In another embodiment, the reaction is conducted in an ionic liquid medium. Exemplary ionic liquids are described below.

Metal hydride catalysts may be added to the reaction mixture. Exemplary metal hydrides are hydrides of Group 1 and Group 2 metals, including but not limited to NaH, KH, LiH, $CaH_2$, $MgH_2$, and the like.

Furthermore, ligands containing at least two heteroatoms selected from O, N and S may also be present in the reaction mixture. For example, the ionic liquid may be a ligand-containing ionic liquid, wherein the ligand may be present in the $R^1$—$R^8$ groups.

In one embodiment, the catalyst is NaH and the ligand is a crown ether or a triamine, such as diethylene triamine and other alkylene triamines.

In another embodiment, the ionic liquid has been functionalised to incorporate a donor moiety, conveying ligand-like properties to the ionic liquid. More specifically, the functionlaised ionic liquid contains a tethered ligand having at least three heteroatoms independently selected from O, N and S; for example, the tethered ligand is a tethered ether linkage.

When ionic liquid is used, the reaction temperature is preferably from about 25 to 80° C. If present, the amount of ligand-containing material, such as a crown ether or a triamine, ranges from about 25% to about 50% by weight of the reaction mixture.

Aldol Process

A process for producing β-hydroxyalkyl cyclohexenyl ketone is described below. Specifically, the process involves combining an alkyl cyclohexenyl ketone with an aldehyde in the presence of a metal halide catalyst, and epimerizing the alkyl cyclohexenyl ketone, thereby producing a β-hydroxy alkyl cyclohexenyl ketone; the process is conducted in the presence of a ligand which has at least two heteroatoms independently selected from O, N and S.

Exemplary aldehydes are linear or branched, C2-C6 aliphatic aldehydes.

Exemplary catalysts are metal hydrides of Group 1 or Group 2 metals, such as NaH, KH, LiH, $CaH_2$, $MgH_2$, and the like.

Exemplary ligands are crown ethers, triamines, and an ionic liquid comprising a ligand, more specifically, a tethered ligand having at least three heteroatoms independently selected from O, N and S. Exemplary triamines include diethylene triamine, 1,4,7-triaza heptane, or methylated derivatives thereof, such as 1,4,7-triaza-1,1,4,7,7-pentaalkyl heptane.

In one embodiment, ethanal and 2,6,6-trimethylcyclohexenyl methyl ketone are combined to produce the resulting product—a methyl trimethylcyclohexenyl ketone.

In another embodiment, the process is conducted in the presence of NaH and a crown ether, more specifically, 18-crown-6.

In another embodiment, the process in conducted in the presence of NaH and an ionic liquid containing a tethered ligand, more specifically, the tethered ligand is a tethered ether linkage.

The reaction temperature is preferably from about 25 to 80° C. throughout the entire process. If present, the amount of ligand-containing material ranges from about 25% to about 50% by weight of the reaction mixture.

Dehydration of the Aldol Addition Product

β-hydroxy alkyl cyclohexenyl ketone produced by the above processes may further undergo a dehydration step to convert it to an enone, more specifically, δ-damascone.

The dehydration step can be conducted by exposing the reaction to air or vacuum at a temperature ranging from about 10° C. to about 30° C. Optionally, common dehydrating agents such as p-toluenesulfonic acid can be used.

Thus, the novel epimerisation process of the present invention can be used to provide a complete process for synthesising δ-damascone from alkyl cyclohexene ketones.

Synthesis of Delta Damascene

In one embodiment, the process comprises the steps of:

a first step of combining an alkylcyclohexenyl ketone with an aldehyde in the presence of metal hydride; and epimerising the alkylcyclohexenyl ketone, thereby producing a P-hydroxy alkyl cyclohexenyl ketone; and a second step of dehydrating P-hydroxy alkylcyclohexenyl ketone, thereby converting it to an enone.

In another embodiment, the process comprises the steps of:

a first step of reacting an epimerisable cyclohexenyl ketone with a metal hydride, wherein this step is conducted in a crown ether, a triamine, an ionic liquid containing a ligand, or mixtures thereof;

a second step combining an alkyl cyclohexenyl ketone with an aldehyde in the presence of metal hydride; and epimerising the alkyl cyclohexenyl ketone, thereby producing a P-hydroxy alkyl cyclohexenyl ketone; and a third step of dehydrating β-hydroxy alkyl cyclohexenyl ketone, thereby converting it to an enone.

Ionic Liquids

The term "ionic liquid" as used herein refers to a salt that has a melting temperature of about 100° C. or less, alternatively of about 60° C. or less, or in a further alternative, of about 40° C. or less. Some ionic liquids exhibit no discernible melting point (based on DSC analysis) but are "flowable" (or glassy) at a temperature of about 100° C. or below; other ionic liquids are "flowable" at a temperature of from about 20 to about 80° C. As used herein, the term "flowable" means that the ionic liquid exhibits a viscosity of less than about 10,000 mPa·s at temperatures of 6 about 100° C. or below or from about 20 to about 80° C. Thus, the "fluid state" of an ionic liquid is meant to encompass all of these embodiments, including the molten state and the flowable state.

It should be understood that the terms "ionic liquid", "ionic compound", and "EL" refer to an ionic liquid, an ionic liquid composite, or mixtures (or cocktails) of ionic liquids. An ionic liquid comprises of an anionic component and a cationic component for charge neutrality. When the ionic liquid is in its liquid form, these components will freely associate with one another (i.e., in a scramble). As used herein, the term "cocktail of ionic liquids" refers to a mixture of two or more, preferably at least three, different and charged EL components, wherein at least one IL component is cationic and at least one EL component is anionic. These binary, ternary or more complex mixtures of ionic liquids (each mixture being a unique and definable ionic liquid in its own right) may be prepared by mixing individual ionic liquids having differing IL components, a more refined version of which is via combinatorial chemistry techniques. Such combinations and their preparation are discussed in further detail in US 2004/0077519A1 and US 2004/0097755A1. As used herein, the term "ionic liquid composite" refers to a mixture of a salt (which can be solid at room temperature) with a proton donor Z (which can be a liquid or a solid) as described in the references immediately above. Upon mixing, these components turn into an ionic liquid that melts or flows at about 100° C. or less.

The ionic liquid useful in the present invention comprises a cationic component having the following formula:

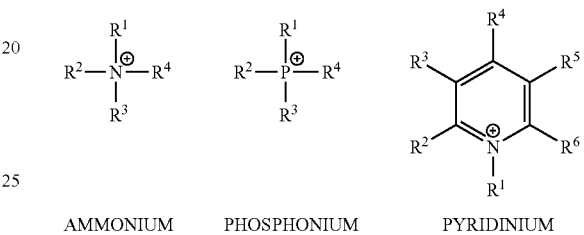

AMMONIUM    PHOSPHONIUM    PYRIDINIUM

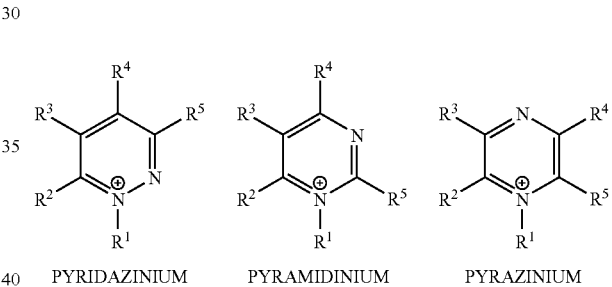

PYRIDAZINIUM    PYRAMIDINIUM    PYRAZINIUM

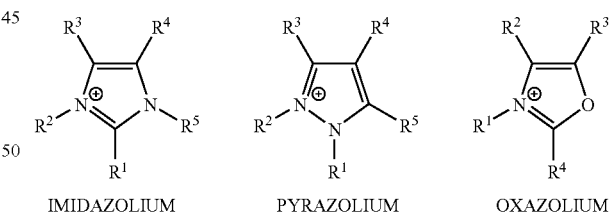

IMIDAZOLIUM    PYRAZOLIUM    OXAZOLIUM

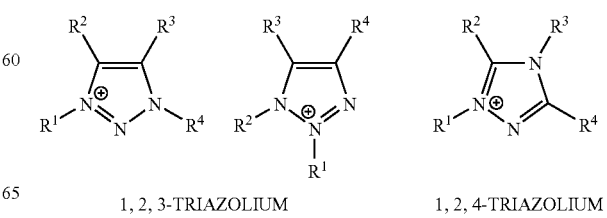

1, 2, 3-TRIAZOLIUM    1, 2, 4-TRIAZOLIUM

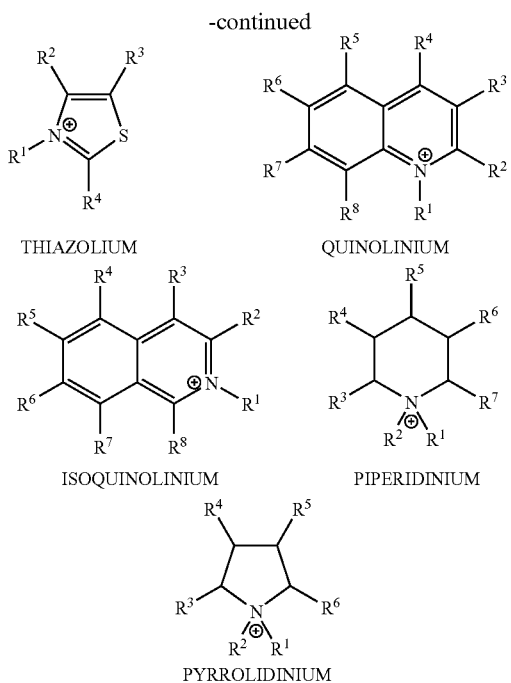

wherein $R^1$—$R^8$ are independently selected from the group consisting of C1-C6 alkyl, alkenyl, hydroxyalkyl, haloalkyl, alkoxylalkyl; C6-C10 aryl or C8-C16 alkylenearyl; and mixtures thereof.

The ionic liquid useful in the present invention comprises an anionic component, which when paired with the cationic component would form an ionic liquid. The anionic component is selected from the group consisting of halogens, C1-C16 carboxylates, C1-C16 alkyl sulfates, mono- or di-C1-C10 alkyl sulfosuccinates, mono- or di-C1-C10 ester sulfosuccinates, and mixtures thereof.

In some embodiments, the cation of the ionic liquid comprises a tethered ligand having the formula:

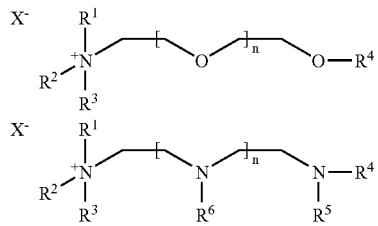

wherein the substitutens $R^1$—$R^6$ are independently C1-C6 alkyl groups, preferably methyl groups; and n is an integer from 1 to 4, preferably 1 to 2. In one embodiment, at least one R substitutent is an alkyl group other than a methyl group while the other R substituents are methyl groups to maintain some degree of asymmetry in the cation; and the anionic component X is a halide or a C1-C6 alkyl, alkenyl, hydroxyalkyl, or haloalkyl moiety.

Typically, ionic liquids may have high viscosities (greater than about 1000 mPa·s) at room temperature. The high viscosities can be problematic in formulating products. Therefore, in specific embodiments of the present invention, the ionic liquid or cocktail of ionic liquids (undiluted with adjuncts, co-solvents or free water) have viscosities of less than about 750 mPa·s, preferably less than about 500 mPa·s, as measured at 20° C. In some embodiments, the viscosity of undiluted ionic liquids are in the range from about 0.1 to about 400 mPa·s, preferably from about 0.5 to about 300 mPa·s, and more preferably from about 1 to about 250 mPa·s.

The viscosities of the ionic fluids can be measured on a Brookfield viscometer model number LVDVII+ at 20° C., with spindle no. S31 at the appropriate speed to measure materials of different viscosities. Typically, the measurement is done at a speed of 12 rpm to measure products of viscosity greater than about 1000 mPa·s; 30 rpm to measure products with viscosities between about 500 mPa·s to about 1000 mPa·s; and 60 rpm to measure products with viscosities less than about 500 mPa·s. The undiluted state is prepared by storing the ionic liquids or cocktails in a desiccators containing a desiccant (e.g. calcium chloride) at room temperature for at least about 48 hours prior to the viscosity measurement. This equilibration period unifies the amount of innate water in the undiluted samples.

EXAMPLES

Example 1

Synthesis Process using KH as the Base

Potassium hydride (1.15 g, 30% slurry, 9.5 mmol) is added to a flask containing cis-4-acetyl-3,5,5-trimethylcyclohexene (1.66 g, 10 mmol) in anhydrous THF (20 ml); the reaction mixture is heated under reflux. Small aliquots of samples are withdrawn at regular intervals, washed with water-hexane and the organic layer is analysed by a gas chromotography (GC). After heating under reflux with KH for about 6 hours, a complete conversion to trans-isomer is observed.

Example 2

Synthesis Process using NaH and 18-crown-6 as the Base

Sodium hydride (0.07 g of 60% NaH in oil, 1.8 mmol) is added, in one portion at 20° C., to a flask containing cis-4-acetyl-3,5,5-trimethylcyclohexene (0.34 g, 2 mmol) with 18-crown-6 (0.13 g, 0.25 mmol, 25 mol %) in 2ml dry THF. Gas evolution is seen straight away. This reaction flask is heated at 80° C. under $N_2$ for 3 hours and monitored by GC. About 96% conversion to trans-isomer is observed after 2 hours.

Example 3

Synthesis Process using NaH/PMDETA

Sodium hydride (40 mg of 60% NaH in oil, 1 mmol) is added, in one portion at 20° C., to a flask containing cis-4-acetyl-3,5,5-trimethylcyclohexene (0.17 g, 1 mmol) in PMDETA (1 ml). Yellow coloration is seen straight away. The reaction mixture is heated at 80° C. under $N_2$ and monitored by GC. About 96% conversion to trans-isomer is observed after 18 hours. Example 4: synthesis process using NaH/BIL-6

Sodium hydride (0.07 g of 60% NaH in oil, 1.8 mmol) is added, in one portion at 20° C., to a flask containing cis-4-acetyl-3,5,5-trimethylcyclohexene (0.34 g, 2 mmol) dissolved in BIL6 (0.5ml). Gas evolution is seen straight away.

This reaction pot is heated at 80° C. under $N_2$ and monitored by GC. About 47% conversion to trans-isomer was observed after 18 hours.

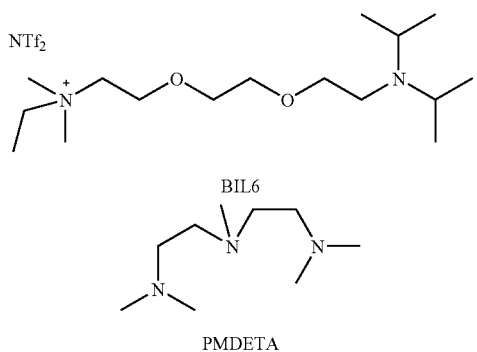

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for epimerizing a cyclohexenyl ketone comprising the step of reacting epimerizable cyclohexenyl ketone with a metal hydride.

2. A process according to claim 1 wherein the metal hydride is a hydride of Group 1 or Group 2 metals.

3. A process according to claim 1 wherein the metal hydride is selected from the group consisting of LiH, NaH, KH, $CaH_2$ and mixtures thereof.

4. A process according to claim 1 wherein the process is conducted in the presence of a ligand which has at least 2 heteroatoms independently selected from O, N and S.

5. A process according to claim 4 wherein the hydride is NaH and the ligand is a crown ether.

6. A process according to claim 5 wherein the crown ether is 18-crown-6.

7. A process according to claim 1 wherein the process is conducted in an ionic liquid medium.

8. A process according to claim 7 wherein the metal hydride is a hydride of Group 1 or Group 2 metals.

9. A process according to claim 7 wherein the process is conducted in the presence of a ligand which has at least 2 heteroatoms independently selected from O, N and S.

10. A process according to claim 9 wherein the hydride is NaH and the ligand is a crown ether or a triamine.

11. A process according to claim 10 wherein the crown ether is 18-crown-6 or the triamine is a diethylene triamine, 1,4,7-triazaheptane, or methylated derivatives thereof.

12. A process according to claim 7 wherein the ionic liquid comprises a cationic component having the following formula:

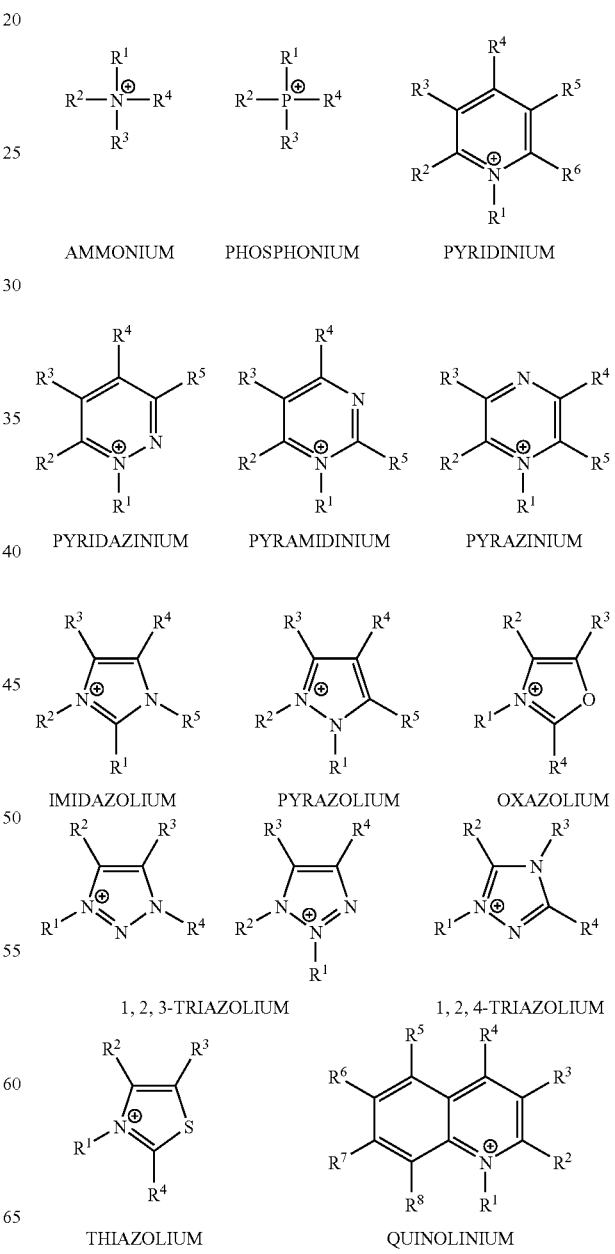

-continued

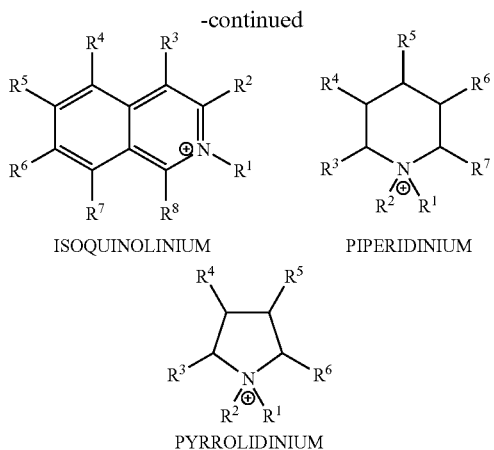

ISOQUINOLINIUM    PIPERIDINIUM

PYRROLIDINIUM wherein $R^1$-$R^8$ are independently selected from the group consisting of C1-C6 alkyl, alkenyl, hydroxyalkyl, haloalkyl, alkoxylalkyl; C6-C10 aryl or C8-C16 alkylenearyl; and mixtures thereof; and an anionic component selected from the group consisting of halogens, C1-C6 carboxylates, C1-C6 alkyl sulfates, mono- or di- C1-C10 alkyl sulfosuccinates, mono- or di- C1-C10 ester sulfosuccinates, and mixtures thereof.

13. A process according to claim 12 wherein the cation of the ionic liquid comprises a ligand.

14. A process according to claim 13 wherein the ligand is a tethered ligand having at least three heteroatoms independently selected from O, N and S.

15. A process according to claim 14 wherein the tethered ligand is tethered ether linkage.

16. A process for making β-hydroxy alkyl cyclohexenyl ketone comprising the steps of
combining an alkyl cyclohexenyl ketone with an aldehyde in the presence of metal hydride; and
epimerizing the alkyl cyclohexenyl ketone, thereby producing a β-hydroxy alkyl cyclohexenyl ketone;
wherein the process is conducted in the presence of a ligand which has at least 2 heteroatoms independently selected from O, N and S.

17. The process according to claim 16 wherein the aldehyde is a linear or branched C2-C6 aliphatic aldehyde.

18. The process according to claim 16 wherein alkyl cyclohexenyl ketone comprises a methyl trimethylcyclohexenyl ketone.

19. The process according to claim 16 wherein the metal hydride is a hydride of Group 1 or 2 metals and the ligand is a crown ether, a triamine, an ionic liquid containing a ligand, or mixtures thereof.

20. The process according to claim 19 wherein the metal hydride is NaH and the ligand is a crown ether.

21. The process according to claim 19 wherein the metal hydride is NaH and the ligand is an ionic liquid containing a tethered ligand.

22. The process according to claim 21 wherein cation of the ionic liquid contains a tethered ligand which has at least three heteroatoms independently selected from O, N and S.

23. The process according to claim 21 wherein the tethered ligand is a tethered ether linkage.

24. The process according to claim 16 further comprising an additional step of dehydrating β-hydroxy alkyl cyclohexenyl ketone, thereby converting it to an enone.

25. The process according to claim 24 wherein the dehydration step is accomplished at a temperature ranging from about 10° C. to about 30° C.

* * * * *

UNITED STATES PATENT AND TRADEMARK OFFICE
CERTIFICATE OF CORRECTION

PATENT NO. : 7,414,158 B2 Page 1 of 1
APPLICATION NO. : 11/880509
DATED : August 19, 2008
INVENTOR(S) : Yousef Georges Aouad et al.

It is certified that error appears in the above-identified patent and that said Letters Patent is hereby corrected as shown below:

<u>Column 3</u>
Line 20, delete "P-hydroxy" and insert -- β-hydroxy --.

<u>Column 5</u>
Line 24, delete "Delta Damascene" and insert -- Delta-Damascone --.
Line 28, delete "P-hydroxy" and insert -- β-hydroxy --.
Line 30, delete "P-hydroxy" and insert -- β-hydroxy --.
Lines 39-40, delete "P-hydroxy" and insert -- β-hydroxy --.
Line 54, delete "6".
Line 59, delete ""EL"" and insert -- "IL" --.
Line 66, delete "EL" and insert -- IL --.

<u>Column 6</u>
Line 1, delete "EL" and insert -- IL --.

Signed and Sealed this

Ninth Day of June, 2009

JOHN DOLL
*Acting Director of the United States Patent and Trademark Office*